(12) United States Patent
Hartman et al.

(10) Patent No.: US 7,058,991 B2
(45) Date of Patent: Jun. 13, 2006

(54) VENTED EYEWEAR

(75) Inventors: James Hartman, Santa Monica, CA (US); Alex Fernandez, Huntington Beach, CA (US)

(73) Assignee: Utopia Optics International, Inc., Redondo Beach, CA (US)

( * ) Notice: Subject to any disclaimer, the term of this patent is extended or adjusted under 35 U.S.C. 154(b) by 0 days.

(21) Appl. No.: 11/014,649

(22) Filed: Dec. 15, 2004

(65) Prior Publication Data

US 2005/0268385 A1    Dec. 8, 2005

Related U.S. Application Data

(63) Continuation-in-part of application No. 10/830,519, filed on Apr. 22, 2004, now Pat. No. 6,964,067.

(51) Int. Cl.
*A61F 9/02* (2006.01)

(52) U.S. Cl. ............................................. 2/437; 2/453

(58) Field of Classification Search .................... 2/429, 2/431, 434, 436, 437, 441, 443, 453
See application file for complete search history.

(56) References Cited

U.S. PATENT DOCUMENTS

| | | |
|---|---|---|
| 2,718,007 A | 9/1955 | Schauweker |
| 3,016,543 A | 1/1962 | Lindblom |
| 3,276,034 A | 10/1966 | Cupp |
| 3,782,810 A | 1/1974 | Marker ........................ 351/47 |
| 4,724,546 A | 2/1988 | Cumbie, Jr. ...................... 2/12 |
| 4,901,374 A | 2/1990 | VanderWoude .................. 2/10 |
| 5,347,655 A | 9/1994 | Garrett ............................ 2/10 |
| D377,036 S | 12/1996 | Leonardi ................... D16/304 |
| 5,652,954 A | 8/1997 | Paiement et al. ................ 2/10 |
| 5,711,035 A * | 1/1998 | Haslbeck ........................ 2/436 |
| 5,752,280 A | 5/1998 | Hill .............................. 2/453 |
| D408,431 S | 4/1999 | Simioni .................... D16/312 |
| 6,178,561 B1 | 1/2001 | Cheng ........................... 2/431 |
| 6,357,053 B1 | 3/2002 | Wang Lee ..................... 2/431 |
| D457,909 S | 5/2002 | Wang-Lee .................... D16/6 |
| D477,010 S | 7/2003 | Moritz et al. .............. D16/312 |
| 6,637,038 B1 * | 10/2003 | Hussey .......................... 2/436 |
| 6,665,885 B1 * | 12/2003 | Masumoto ..................... 2/436 |
| 6,692,124 B1 * | 2/2004 | Katz et al. .................... 351/62 |

* cited by examiner

*Primary Examiner*—John J. Calvert
*Assistant Examiner*—Brian Kauffman
(74) *Attorney, Agent, or Firm*—Cislo & Thomas, LLP

(57) ABSTRACT

An eye protection device is disclosed herein. The eye protection device includes an open face frame, a lens frame with a lens coupled thereto, and means for coupling the lens frame to the open face frame, wherein the lens frame, if pivotally coupled, may be selectively positionable with respect to the open face frame, and has one or more antifogging passageways.

26 Claims, 9 Drawing Sheets

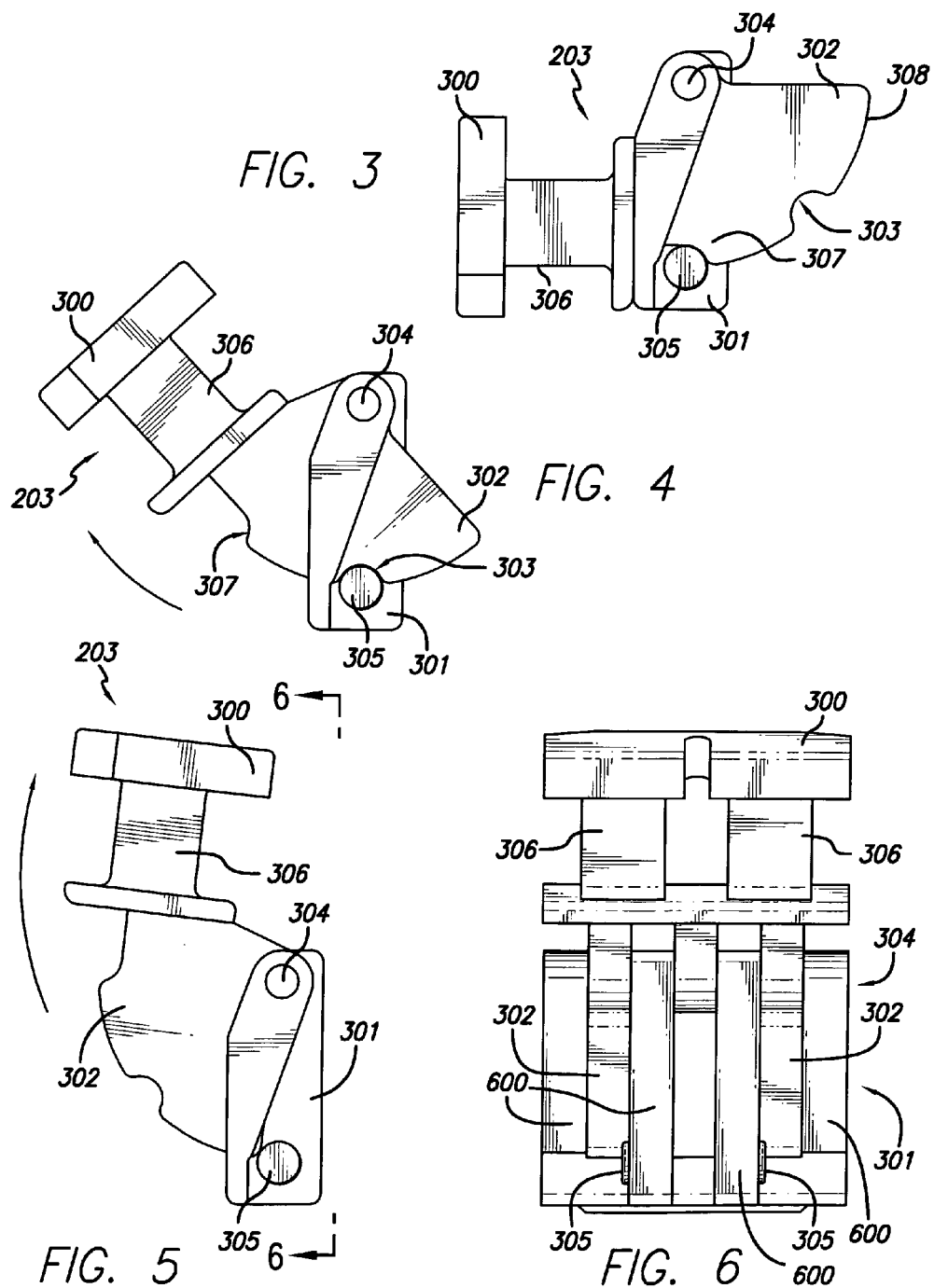

VENTED EYEWEAR

REFERENCE TO RELATED APPLICATION

This application is a continuation-in-part of application Ser. No. 10/830,519 filed Apr. 22, 2004 now U.S. Pat. No. 6,964,067, for a Hinged Goggle, the substance of which is hereby incorporated by reference.

BACKGROUND

Various types of eye protection devices have developed in the prior art such as goggles, eyeglasses, visors, shields, or the like. These goggles may be used in a variety of applications such as, but not limited to, manufacturing or recreational purposes. With respect to recreational uses, various goggles have been developed for skiing, snowboarding, or other activities where the user intends to protect one's eyes. In the prior art, goggles have been developed where a portion of the goggle may be flipped up so that the lens portion of the goggle is removed from the user's line of sight. While these prior art goggles having a moveable lens are useful, there still remains a need for an eye protection device such as a goggle wherein a portion of the goggle remains fixed to the user's face when the lens is flipped up or otherwise moved out of the user's line of sight.

SUMMARY

Exemplary embodiments disclosed herein are directed to eye protection devices having a lens frame and an associated lens that is coupled pivotally or otherwise to the face frame such that the frame and associated lens may be "flipped up" or otherwise moved out of the user's line of sight while the face frame remains fixed to the user's face. According to one exemplary embodiment, the eye protection device is composed of a lens frame and associated lens, an open face frame, and a means for coupling the lens frame to the open face frame. In one embodiment the lens frame is pivotally coupled to the open face frame and is selectively positionable with respect to the open face frame.

In another exemplary embodiment, the eye protection device includes a lens coupled to a lens frame, wherein the lens frame is pivotally coupled to a face frame by a hinge. The hinge allows the lens frame to be selectively positionable with respect to the face frame. The eye protection device also includes an adjustable strap having a first end and a second end, wherein the first end of the adjustable strap is coupled to a portion of the face frame and the second end of the adjustable strap is coupled to an opposite portion of the face frame.

Adherence or coupling of the lens frame to the face frame is attained by a variety of means, including but not limited to hinges, magnets, latches, snap friction fit means, Velcro, etc.

BRIEF DESCRIPTION OF THE DRAWINGS

FIG. 1A is an enlarged cross sectional view of the eye protection device of FIG. 1 taken along line 1A—1A;

FIG. 3 is an enlarged side view of the embodiment of a hinge used in the eye protection device of FIG. 1;

FIG. 4 is an enlarged side view of the hinge embodiment of FIG. 3 wherein the hinge is in a partially opened position;

FIG. 5 is an enlarged side view of the hinge embodiment of FIG. 3 wherein the hinge is in a fully opened position; and FIG. 6 is an enlarged rear view of the hinge embodiment in a fully opened position;

DETAILED DESCRIPTION

The detailed description set forth below in connection with the appended drawings is intended as a description of exemplary embodiments and is not intended to represent the only forms in which the exemplary embodiments may be constructed and/or utilized. The description sets forth the functions and the sequence of steps for operating the exemplary embodiments. However, it is to be understood that the same or equivalent functions and sequences may be accomplished by different embodiments that are also intended to be encompassed within the spirit and scope of the specification.

Figure 9:
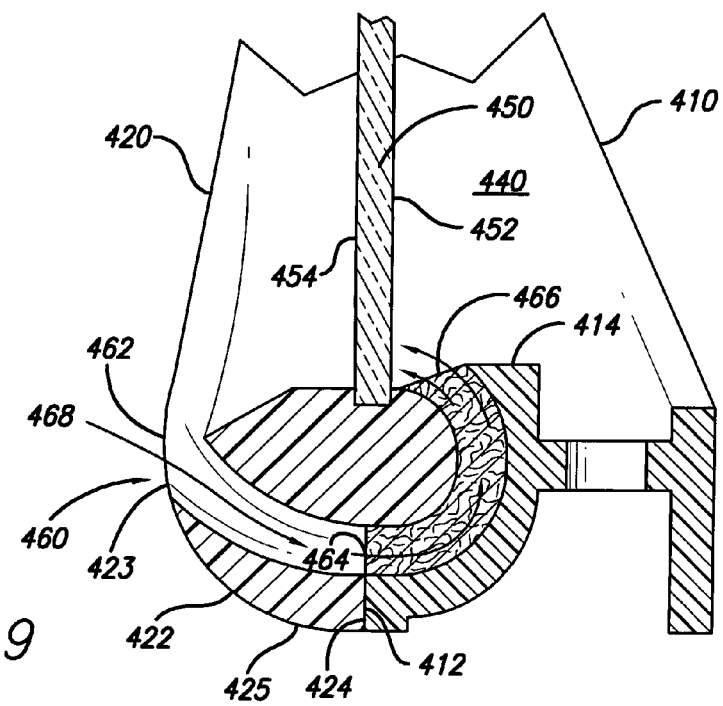
FIG. 9 is an enlarged cross sectional view of the eye protection device of FIG. 7 taken along line 1B—1B.

Additionally, for purposes of clarity foam material that is conventionally found in goggles and the like (particularly snow goggles) has been left out of the drawings with the exception of its showing in one of the unique features of the invention illustrated in FIG. 9.

Figure 7:
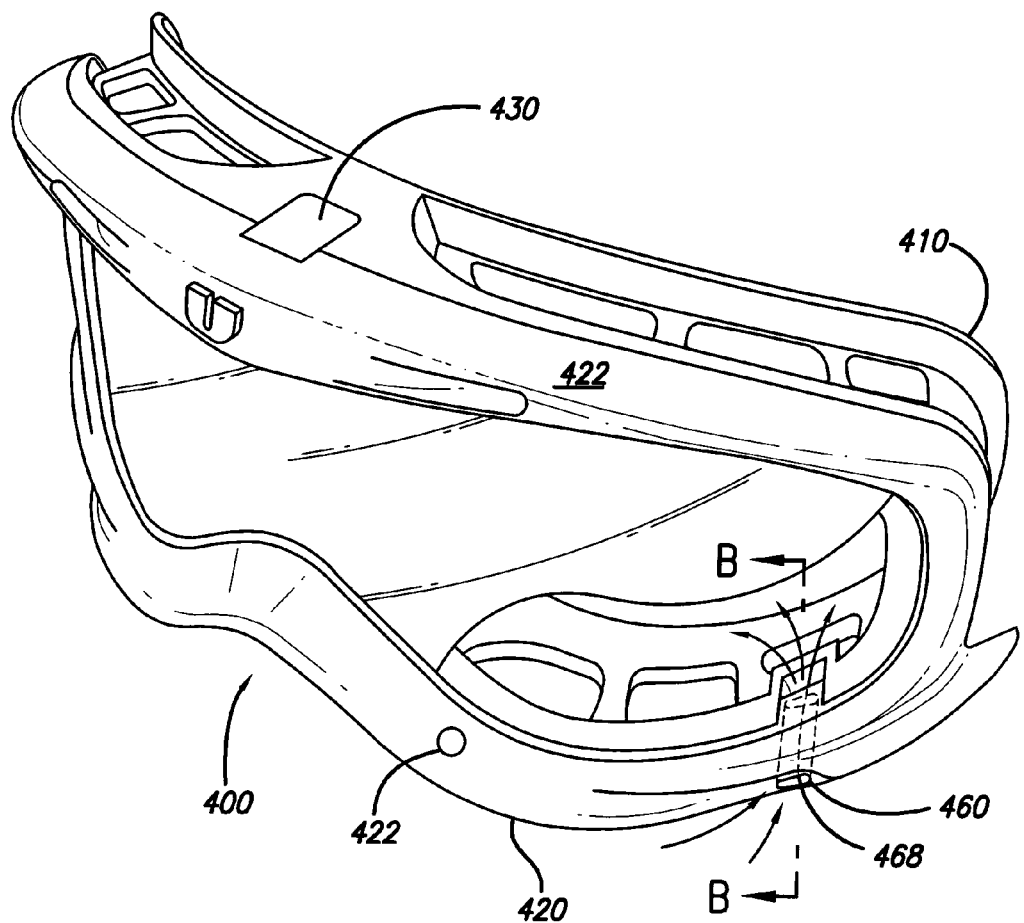
FIG. 7 is a perspective view of an embodiment of an eye protection device showing a tubular air vent for preventing fogging of the lens.

Thus, for example foam insulation of the conventional type would be normally included in face frame lower openings or apertures 205 (FIG. 2) and the unnumbered upper openings on apertures of the face frame (FIG. 7).

Figure 1:
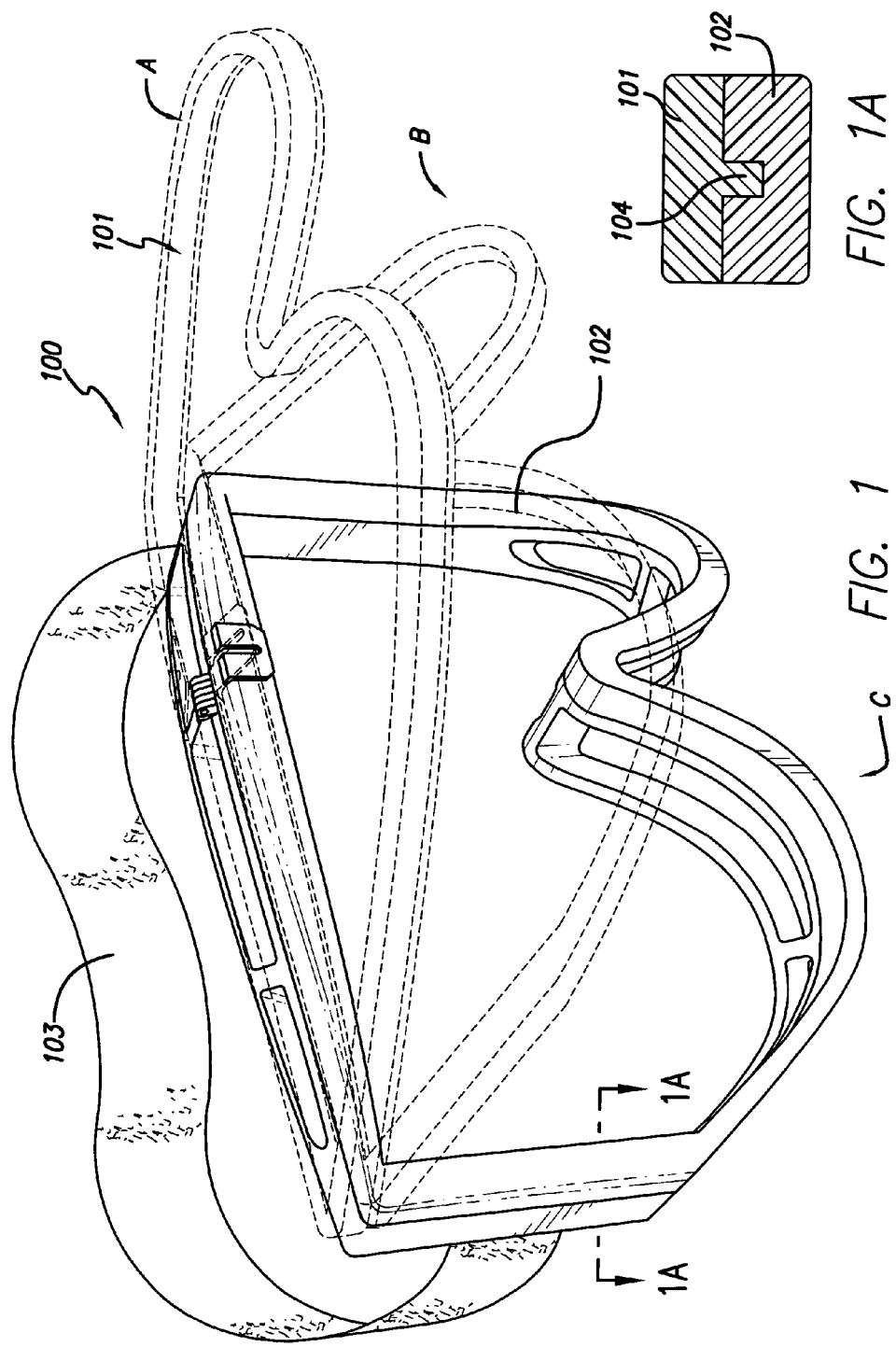
FIG. 1 is a perspective view of one embodiment of an eye protection device wherein the lens frame is selectively positionable with respect to the face frame.

Turning now to the figures, FIG. 1 illustrates one exemplary embodiment of the eye protection device 100. As shown in FIG. 1, the eye protection device 100 includes a face frame 102 and a lens frame 101. An adjustable strap 103 is coupled to opposite sides of the face frame in order to secure the eye protection device 100 to the face of the user. The lens frame 101 may be selectively positional with respect to the face frame 102 at positions A, B, and C. In position A, the lens frame 101 is in an open or upright position such that the lens frame is positioned approximately 90° with respect to the face frame 102. In position B, the lens frame 101 is in spaced relationship to the face frame 102. In one embodiment, the lens frame 101 is at an angle approximately. 45° from the face frame. In position C, the lens frame 101 is positioned such that the lens frame 101 contacts the face frame 102. In other embodiments, the lens frame 101 may be selectively positionable at one or more positions between approximately 1° to approximately 180° with respect to the face frame 102.

When the lens frame 101 is in positions A or B, the user is able to provide additional ventilation to the lens and user's face without removing the eye protection device 100 from the user's face. In another exemplary embodiment, the ability to flip-up the lens frame 101 from the face frame 102 allows the user to remove any polarized or dark lens that may be associated with the lens frame from the user's line of sight. Also, the user may clean the inner surface of the lens without removing the eye protection device 100 from one's face.

Figure 2:
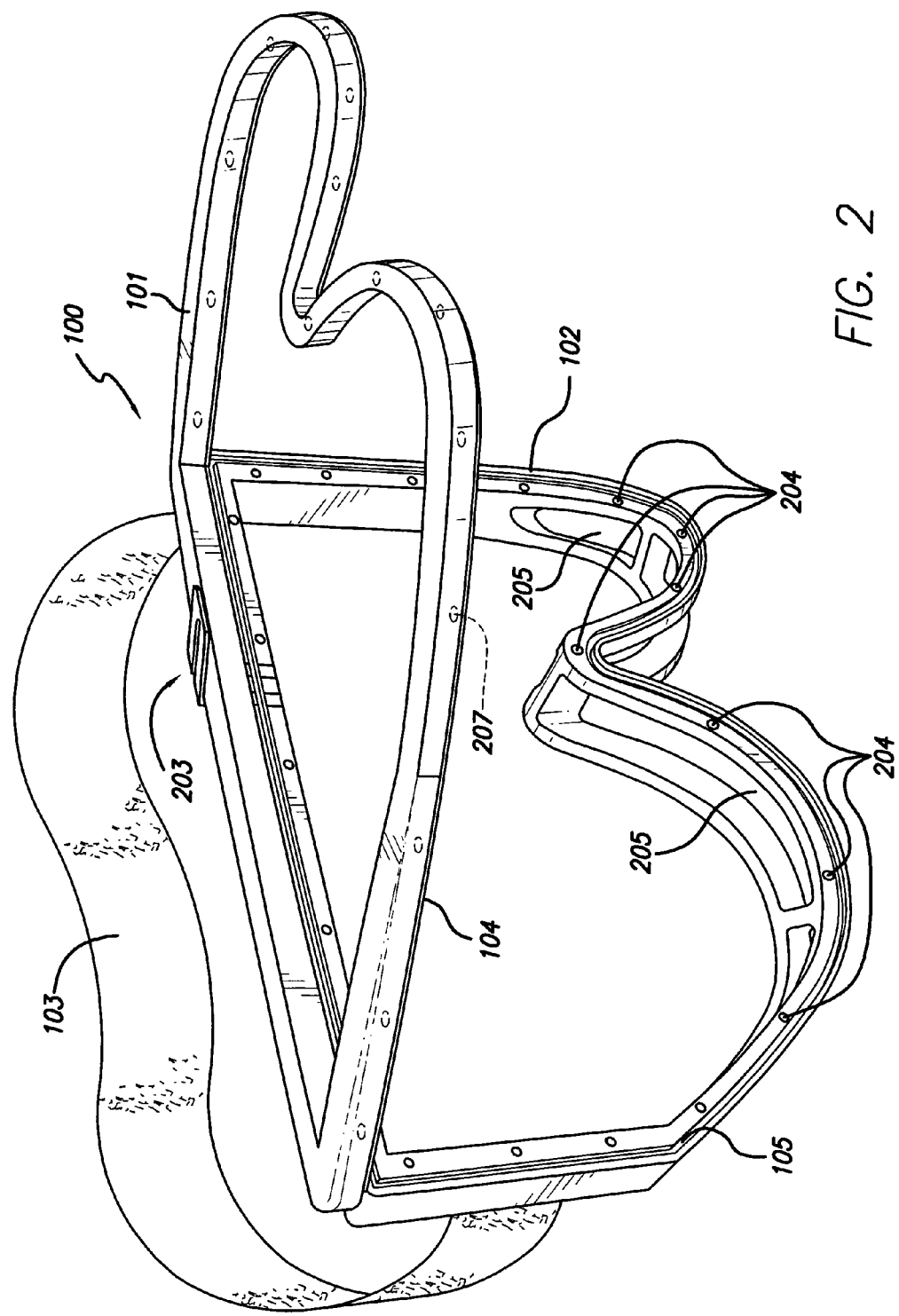
FIG. 2 is a perspective view of the embodiment of FIG. 1 wherein the lens frame is in an open position.

The eye protection device 100 can include a means for sealing the space between the face frame 102 and the lens frame 101 when in position C. The means may be a "tongue" 104 and "groove" 105 interlocking connection as shown in FIG. 2. In other embodiments, the means may be other sealing means known or developed in the art. As those skilled in the art will appreciate, the "tongue" 104 and "groove" 105 interlocking connection may be made of rigid, elastomeric, foam, or any other material suitable for creating an interlocking relationship between two surfaces.

As shown in FIG. 1A, the lens frame 101 and the face frame 102 have corresponding tongue 104 and groove 105 interlocking connection. In one embodiment, the tongue portion 104 or extending ridge is provided on the lens frame 101 and a corresponding groove 105 is provided on the face frame 102. In an alternate embodiment, the tongue portion 104 is provided on the face frame 102 and the groove 105 portion is provided on the lens frame 101. The tongue 104 and groove 105 interlocking connection provided on the periphery of the face frame 102 and lens frame 101 prevent moisture, snow, dirt, and other debris from entering the interior of the eye protection device 100.

FIG. 2 illustrates the eye protection device 100 wherein the lens frame 101 is substantially perpendicular to the face frame 102. As shown in FIG. 2, the face frame 102 includes a generally horizontally-extending brow portion that is coupled to or integral with a generally arcuate shaped bottom that is sized to fit over the user's cheek and nose. Additionally, the face frame 102 includes a plurality of vents 205 that may be positioned about the perimeter of the face frame 102. As shown in FIG. 2, the ventilation ports 205 are positioned on the lower portion of the face frame 102. In an alternate embodiment, the ventilation ports 205 may be positioned at the top of the face frame 102. In yet another embodiment, the ventilation ports 205 may be positioned at both the top and bottom of the face frame 102.

In another embodiment, the ventilation ports 205 may be positioned on the sides of the face frame 102. In yet another embodiment, the ventilation ports on the sides of the face frame 103 may be combined with ventilation ports 205 that are positioned on the top, bottom, or combinations thereof. The ventilation ports 205 are designed to allow moving air to enter the interior of the goggle in order to reduce fogging.

As shown in FIG. 2, the face frame 102 includes a plurality of magnets 204 that are positioned about the periphery of the face frame 102. Additionally, the lens frame 101 includes corresponding magnets 207 that engage the magnets 204 on the face frame. In another embodiment, the face frame material 102 may be magnetized to attract the lens frame material 101 wherein the lens frame includes metal inserts. In another embodiment, the lens frame 101 includes corresponding metal inserts to attract corresponding magnets. In yet another embodiment, face frame material 102 may be magnetized to attract the lens frame material 101. Accordingly, the magnets 204, 207 secure the lens frame 101 to the face frame 102 in a closed position C. That is, the magnets 204, 207 prevent the lens frame 101 from being accidentally dislodged or separated from the face frame 102 of the eye protection device 100. As shown in FIG. 2, the magnets 204, 207 have a generally circular shape, but those skilled in the art will appreciate that the magnets 204, 207 may have a plurality of shapes and sizes. In other embodiments, the magnets 204, 207 may be placed at different locations about the periphery of the face frame 101 and lens frame 102 other than those locations depicted in FIG. 2. As those skilled in the art will appreciate, the lens frame 101 may be releasably securable to the face frame 102 by providing various means of attraction such as, but not limited to, magnet to magnet, magnet to metal, magnetic impregnated plastic, and all other types of magnetic attraction known or developed in the art.

As shown in FIG. 2, the eye protection device 100 also includes a hinge 203. As shown in the embodiment depicted in FIG. 2, the hinge 203 may be affixed to or encapsulated to the top portion of the face frame 102 and a corresponding portion on the lens frame 101. In one exemplary embodiment, the hinge 203 may be positioned on the center of the face frame 102. In another embodiment, the hinge 203 may be offset to one side of the face frame 102. In yet another embodiment, the eye protection device 100 may have one or more hinges 203 positioned on the face frame 102. For instance, in one embodiment, the hinges 203 may be located at the ends of the face frame 102. In another embodiment, the hinges 203 may be centrally positioned on the top portion of the face frame 102. In yet another embodiment, the hinge may be a living hinge consisting of material from both frames 101 and 102 of the eye protection device 100. The hinge may be a living, encapsulated, inserted, affixed, or secured hinge known or developed in the art.

Turning to FIG. 3, the hinge 203 is composed of a first bracket 300 and a second bracket 301. The first bracket 300 is coupled to the lens frame 101 of the eye protection device 100. The second bracket 301 is fixed to the face frame 102 of the eye protection device 100. FIG. 3 illustrates the hinge 203 when the lens frame 101 is in a closed position with respect to the face frame 102 as shown in position C of FIG. 1.

The first bracket 300 includes a lens frame coupling portion 306 and articulating wedge-shaped member 302. As shown in FIG. 3, the lens frame coupling portion 306 and the wedge-shaped member 302 is an integral structure. In another embodiment, the coupling portion 306 and the wedge-shaped member 302 may be separate components that are also fixed together. The wedge-shaped members 302 are generally planar structures having a curved bottom surface 308. The wedge-shaped member 302 includes a plurality of one or more recesses 303, 307 spaced along the curved surface 308 which are sized to engage an interlocking member 305.

As shown in FIG. 6, the first bracket 300 may include any number of coupling structures including two lens frame coupling structures 306 and a plurality of wedge-shaped members 302. In another embodiment, the first bracket 300 may have one frame coupling structure 306 fixed to a plurality of wedge-shaped members 302. In another embodiment, the first bracket 300 may include two wedge-shaped members 302 as shown in FIG. 6. In other embodiments, the first bracket 300 may include one or more wedge-shaped members 302.

As shown in FIG. 6, the second bracket 301 is composed of at least two fingers 600. The fingers 600 are spaced apart and interwoven with the wedge-shaped members 302 of the first bracket 300. The second bracket 301 also includes an interlocking member 305 that extends from the outer surface of at least two fingers 600. As shown in FIG. 6, the fingers 600 of the second bracket 301 are generally spaced apart and are sized to engage the wedge-shaped member 302 of the first bracket 300. These interlocking members 305 engage the recesses 303, 307 that are provided on the wedge-shaped member 302. When the interlocking member 305 is engaged in the recesses 303, 307 the lens frame 101 is then locked into a position relative to the face frame 102. As shown in FIG. 3, the first bracket 300 and a second bracket 301 are pivotally coupled together at a pivot point 304.

FIG. 4 illustrates the hinge 203 when the lens frame 101 is in position B as depicted in FIG. 1. The hinge 203 is now locked as the interlocking member 305 has engaged the recess 303 that is positioned on the curved face 308 on the wedge-shaped member portion 302 of the first bracket 300. The first bracket 300 is pivotable about the pivot point 304 until the recess of 303 and 307 accept the protruding member of 305.

FIG. 5 illustrates the hinge 203 in the fully opened position (position A of FIG. 1). The end of the curved portion 308 has been pivoted beyond the interlocking member 305, and the corner of the wedge-shaped member 302 rests upon the interlocking member 305. As those skilled in the art will appreciate, the hinge 203 may have a plurality of recesses 303 such that the lens frame 101 may be open to various points along the curved portion 308 of the wedge-shaped member 302. The hinge 203 allows the user to move the lens frame 101 with respect to the face frame 102 and lock the lens frame 101 at various positions from the face frame 102.

As shown in FIG. 6, the hinge 203 includes a first bracket 300 and a second bracket 301. The various members 302, 600 of the first bracket 300 and the second bracket 301, respectively, are interwoven and interconnected at a pivot point 304. The respective members 302, 600 of the first and second bracket are adjacent to one another and may or may not have a very small clearance. The small clearance allows the interlocking member 305 to be a relatively small protuberance that extends from the fingers 600 of the second bracket 301.

In yet another embodiment, the hinge 203 may be encapsulated or fixed onto each frame. In yet another embodiment, the hinge 203 may be configured such that the lens and the lens frame 101 may be removable or detached from the face frame 102. Furthermore, as those skilled in the art will appreciate, the hinge 203 does not need to index.

In use, the eye protection device 100 may be used for a myriad of activities where individuals need to protect their eyes from the elements, debris, or objects. For instance, the eye protection device 100 may be used in winter activates such as, but not limited to, skiing, snow-boarding, snow mobiling, snow shoeing, cross country skiing, or the like. Alternatively, the goggles may be used for motor sports such as, but not limited to, motor-cross, racecar driving, or the like. Also, the goggles may be used for but not limited to free diving, snorkeling, or scuba diving. As those skilled in the art will appreciate, the eye protection devices disclosed herein may be utilized in those activities where an individual user desires the use of ones eyes under optimum, ambient conditions.

Figure 8:
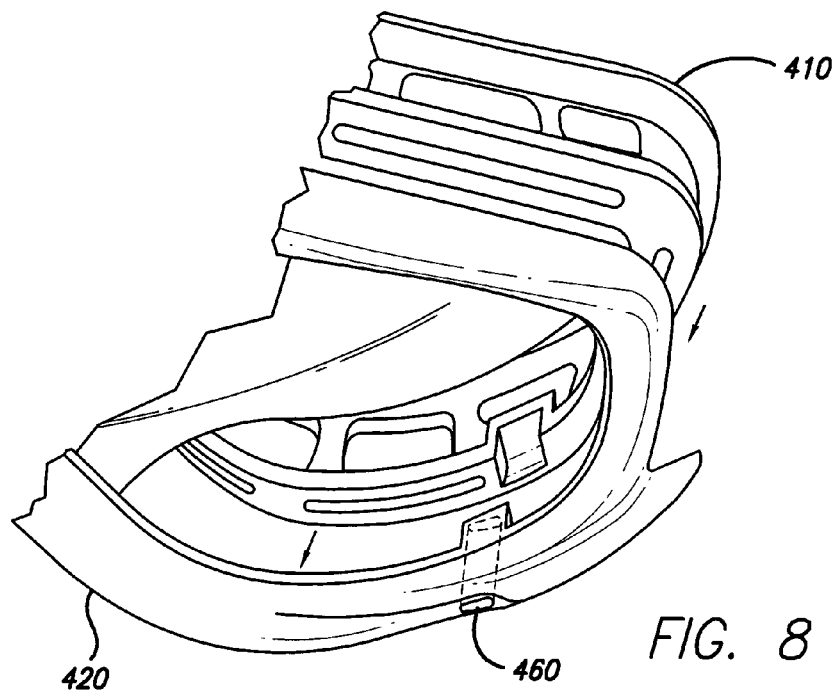
FIG. 8 is an enlarged, partial perspective view of an embodiment of the eye protection device shown in FIG. 7.

FIGS. 7–9 illustrate another embodiment of an eye protection device 400. Like the eye protection devices described above, the eye protection device 400 includes a face frame 410, a lens frame 420 with a lens 450 removably coupled thereto. The face frame 410 and lens frame 420 are coupled via a removably detachable hinge 430. The lens 450 includes an inner face 452 and an outer face 454. As is best seen in FIG. 9, the lens frame 420 includes an exterior or outwardly facing surface 422 and an inwardly disposed mating surface 424 which mates with a similar mating surface 412 on the face frame 410. The face frame 410 also includes an upwardly disposed surface 414 which lies within a cavity 440 bounded by the lens 450 and the face of a person (not shown) wearing the eye protection device 400.

In addition to the features described in the embodiments illustrated above, the eye protection device 400 may include one or more curvilinear passageways 460 having a proximal end or air inlet 462, a midpoint 464, and a distal end or air outlet 466 configured to direct ambient air against face 452 of lens 450 as represented by the arrows. One passageway 460 (without foam filter) is shown in the figures for clarity of illustration, however those skilled in the art will understand that a plurality of passageways 460 is both possible and desirable. Also, passageway 460 may contain a foam filtering agent if desired. The proximal end 462 of the passageway opens upon the outwardly facing exterior surface 422 of the lens frame 420 such that air impinging upon the front of the eye protection device 400 flows into the proximal end 462 of the passageway 460. The passageway 460 may also open radially outwardly on the lens frame 420 along a radially outwardly facing exterior surface 425. The distal end 466 of the passageway 460 opens upon the upwardly disposed surface 414 of the interior of the lens frame 410 and is positioned such that air exiting or discharging from the distal end 466 of the passageway 460 is directed towards the inside face 452 of the lens 450. A foam filtering agent is employed from midpoint 464 to outlet 466 of passageway 460 for its conventional filtering effect as those of ordinary skill in the art will recognize.

The passageway 460 follows a curved path 468 through the lens frame 420 and the face frame 410 of the eye protection device 400 and therefore is formed as two portions, one portion being in the lens frame and the second portion being in the face frame. The portion of the passageway 460 formed in the lens frame 420 is bounded by the proximal end 462 and the midpoint of the passageway 464. The portion of the passageway formed in the face frame 410 is bounded by the midpoint 464 and distal end of the passageway 466. The curved path 468 may be a regular curve such as a generally u-shaped or similar curve or may be an irregular curve. However, the curved path should include curvature within a range of about 15 to about 90 degrees, though greater or lesser amounts of curvature may also prove suitable. The curvature in the passageway creates a ram-pressure effect whereby air is accelerated as it travels through the passageway.

As stated above, the curved path 468 should be configured such that air entering from the proximal end 462 is generally directed to discharge from the distal end 466 onto the inside face 452 of the lens 450. In the exemplary embodiment, the distal end of the passageway 466 is angled about 15 degrees from vertical towards the inside face of the lens 452. The passageways may be angled within a range from about 5 degrees from vertical to about 84 degrees from vertical within which anti-fogging performance is acceptable. Other more extreme angles may also be suitable. Also, the passageway 460 may taper from its proximal end 462 to its distal end 466. In other words, the proximal opening 462 may be larger than the distal opening 466. The taper may extend over all or a portion of the length of the passageway 460. The taper in the passageway causes the passageway 460 to function as a venturi whereby air is accelerated during its travel through the passageway.

In use, air is directed towards the front face of the lens 454 by air pressure caused by forward movement of an individual wearing the eye protection device 400. For example, when an individual skis down a slope air pressure builds up on the front face of the lens 454. Thus, air pressure forces air to flow through the one or more passageways 460. As described earlier, the passageway 460 is configured such that air entering the passageway at its proximal end 462 is directed to exit the distal end 466 such that the air is directed against the inside face 452 of the lens 450 and thereby prevents the lens from fogging while in use. The air flowing through the passageway is accelerated due to the venturi and ram-pressure effects created by the taper and curvature of the passageway. The configuration of the vents control the speed and direction of the air entering the eye protection device. The air is directed at specific angles to intersect the interior of the lens where fogging is most prevalent. Additionally, this system creates two vortexes that spin in opposite directions within the internal microclimate of the eye protection device. Consequently, the moisture released from the rider's perspiration is caught in these two vortexes and as a result of centrifugal force, it is whipped outwards towards the peripheral ejection vents where the moisture latent particles are expelled—never condensing into fog. This unique configuration of the passageways 460 of the eye protection device 400 represents an improvement over prior art eye protection devices which have a marked tendency to fog during intense athletic exertion by the wearer.

The cross-sectional shape of the passageway 460 may be of any shape which allows air to flow through the passageway. In other words, the cross sectional shape of the passageway 460 can be an irregular shape or can be of a regular shape. For example, round, oval, or ellipsoidal configurations are just a few of the many possible configurations for the passageway cross section. Likewise the number, size, and spacing of the passageways 460 around perimeter of the lens frame 420 is a matter of design choice. For example, passageways may be spaced along the bottom of the lens frame only, or along the top only, or along the sides only, or in any combination of the above. Similarly, the passageways 460 may be regularly or irregularly spaced.

Other features of the eye protection device 400 include the removably detachable hinge 430. The hinge 430 need not be permanently affixed to the face frame 410 or lens frame 420. Rather, it may often be desirable that the hinge be removably detachable from both the face frame 410 and lens frame 420 to allow for replacement in the event the hinge 430 should suffer damage from, for example, falls which frequently occur during activities such as skiing. Detachability may be provided by designing the hinge 430 as a snap in unit in the face and lens frames 410 and 420 respectively, or by means of attachment screws, or by other fastening means known in the art, clips being one such example.

Figure 10:
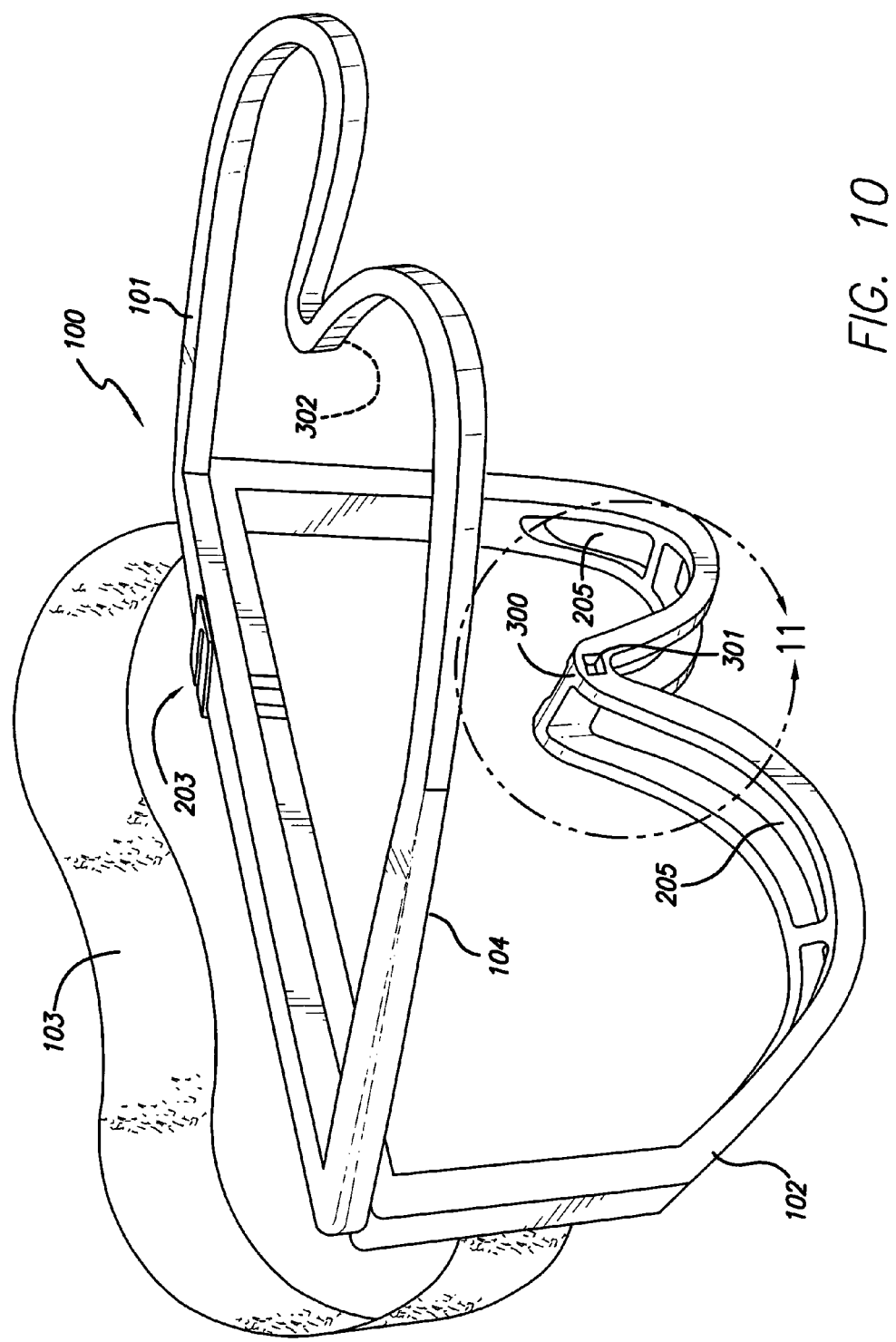
FIG. 10 is a perspective view of another embodiment of the eye protection device wherein a snap friction fit closure is utilized.
Figure 11:
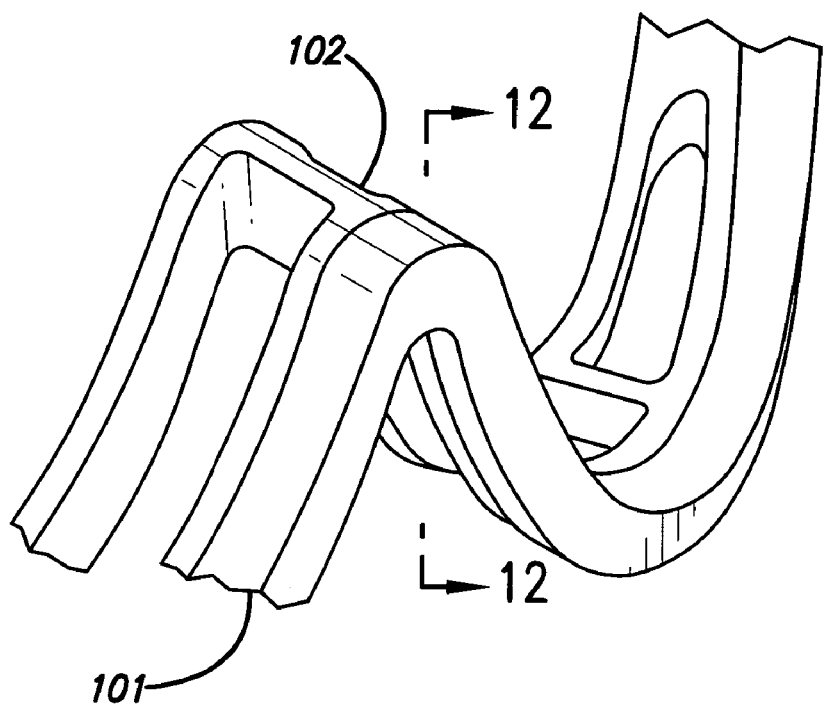
FIG. 11 is an enlarged fragmentary view of still another closure means of the eye protection device taken along the line 11 of FIG. 10.
Figure 12:
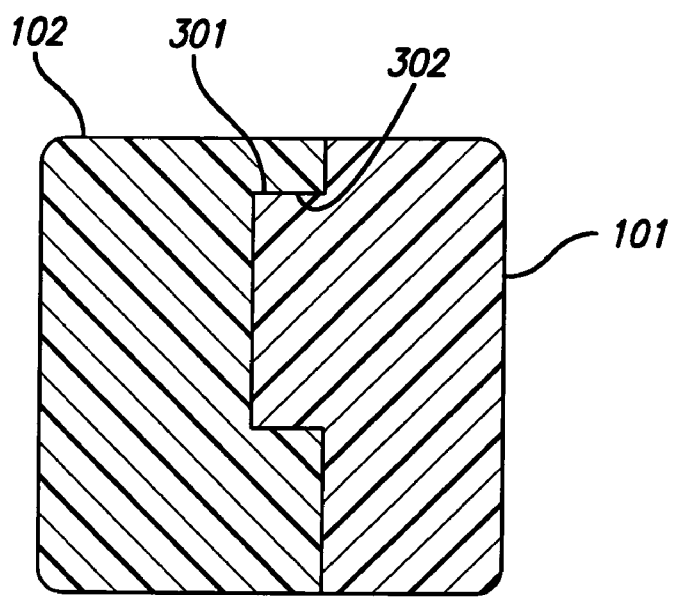
FIG. 12 is a view taken along the line of 12—12 of FIG. 11.

Referring to FIGS. 10, 11 and 12 it will be noted that the eye protection device 100 in this instance has the hinged coupling means 203 but instead of having spaced magnets or the like for securing the lens frame 101 to the open face frame 102 by means of magnets, etc., there is provided in the nose portion 300 a recess opening or aperture 301 which acts as a snap fit closure for the protuberance 302. Thus, when the lens frame 101 is pivotally swung downwardly as seen in FIG. 10, the protuberance or projection 302 frictionally engages the aperture or receiving passageway 301 in friction fit retention so as to retain lens frame 101 to the open face frame 102.

Figure 13:
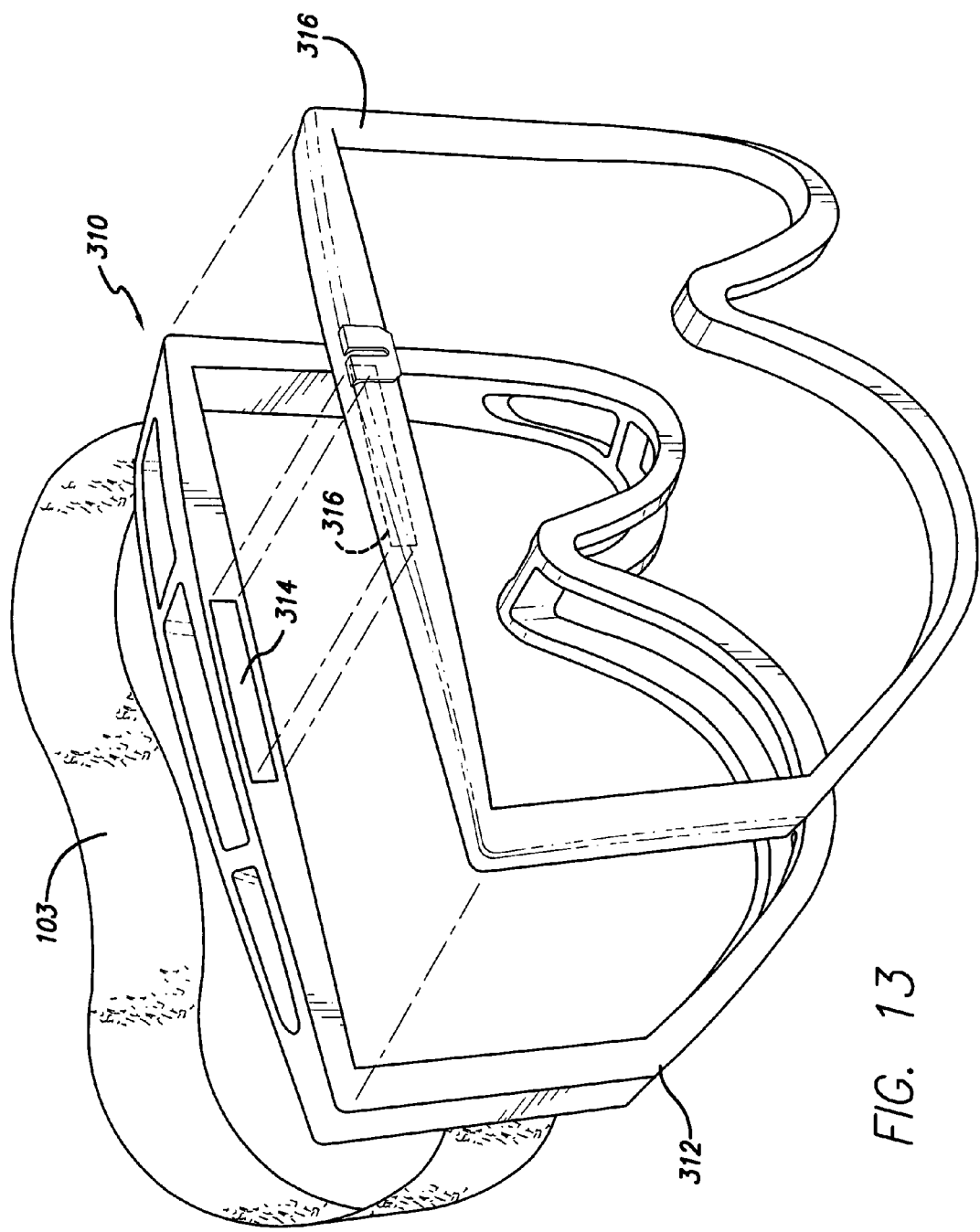
FIG. 13 is a perspective view of still another embodiment of the eye protection device not utilizing a hinged connection to the open face frame.

Referring to FIG. 13, another embodiment of the eye protection device 310 is illustrated wherein in this instance it does not have a hinged attachment but rather the open face frame 312 is provided with a receiving slot or groove 314 and the lens frame member 316 is provided with a congruently shaped protuberance 316 which snaps the lens frame 316 into place with open face frame member 312.

Figure 14:
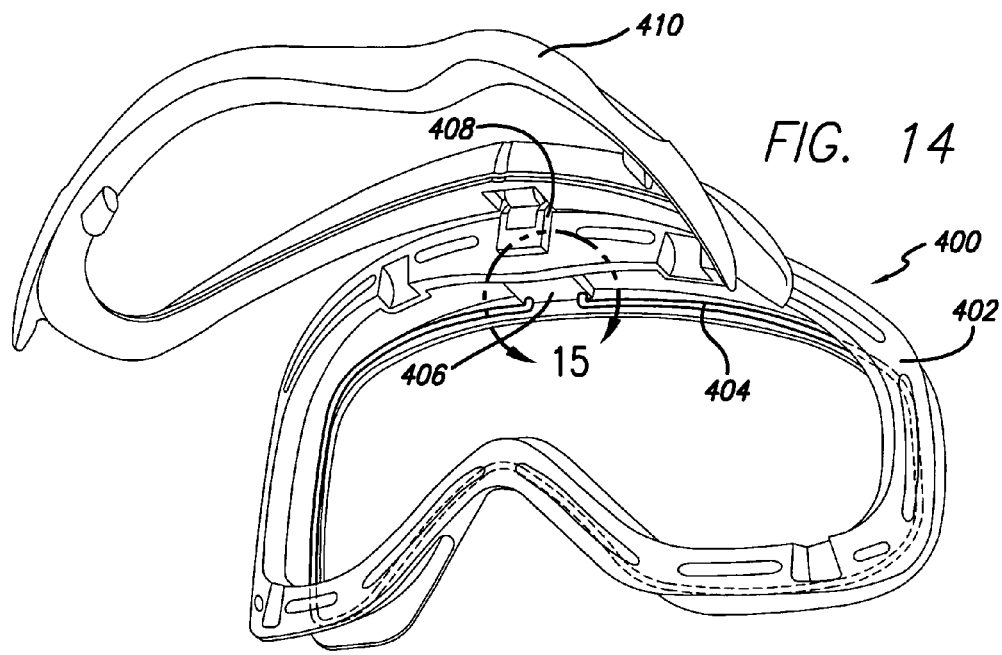
FIG. 14 is a perspective view of still another embodiment of the eye protection device showing a force dissipating wire member for the hinge.
Figure 15:
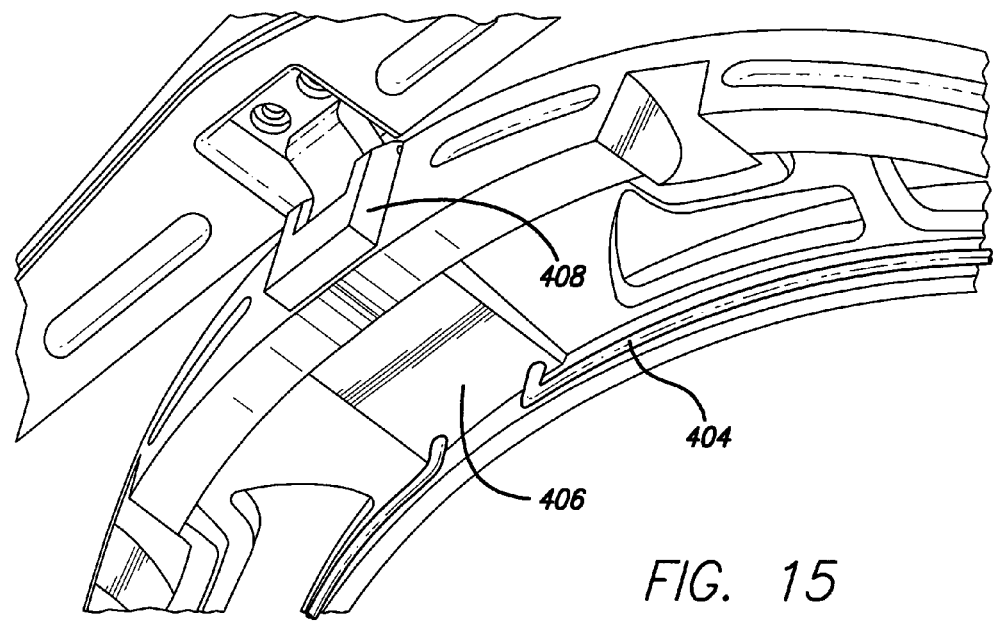
FIG. 15 is a view taken along the line 15 of FIG. 14.

Referring to FIGS. 14 and 15, in this instance the eye protection device 400 has incorporated in face frame 402, circumscribing wire element 404 which acts as a stiffener for the face frame 402 which may be of softer plastic material for comfort of the wearer thereby controlling and reducing distortion which would otherwise occur due to the strap pressure caused by the strap (not shown) holding eye protection device 400 to the head of the wearer.

The wire element 404 is also securely affixed to hinge element 406 which acts with cooperating hinge element 408 to hingedly connect face frame 402 with lens frame 410.

Thus, wire element 404 not only acts to control the shape of the face frame 402 and reducing distortion when a softer face frame material is utilized but also acts as a support for the cantilevered load from the hinge support for the lens frame.

Those of ordinary skill in the art will of course recognize the necessity of having the use of various plastic materials that lend themselves to friction snap engagements as alluded to in the FIGS. 10, 11, 12 and 13 embodiments as well as the necessary clearances with respect to protuberance snap button and accommodating receiving and mating aperture or slot.

In closing, it is to be understood that the embodiments described herein are illustrative of the principles of the exemplary embodiment. Thus, by way of example, but not of limitation, alternative configurations or modifications may be utilized in accordance with the teachings herein. Also various coupling means may be used whether they be hinges, magnets, Velcro, snap fit members or any other means, just so long as the end functions of the eyewear of the invention are obtained. Accordingly, the drawings and description are illustrative and not meant to be a limitation thereof.

What is claimed is:

1. An eye protection device, comprising:
   an open face frame;
   a lens frame with a lens coupled thereto;
   a coupling means for coupling the open face frame to the lens frame; and
   at least one passageway formed in the open face and lens frames, the at least one passageway having a curved path, wherein the at least one passageway includes a proximal end configured to receive air and a distal end configured to discharge air upon an interior face of the lens.

2. The eye protection device of claim 1, wherein the at least one passageway is tapered along at least a portion of its length whereby the at least one passageway functions as a venturi.

3. The eye protection device of claim 1, wherein the distal end of the at least one passageway is configured to discharge air upon an interior surface of the lens at an angle from a vertical within a range of about 5 degrees to about 85 degrees.

4. The eye protection device of claim 1, wherein the curved path of the at least one passageway includes about 20 degrees to about 90 degrees of curvature.

5. The eye protection device of claim 1, wherein the curved path of the at least one passageway is generally u-shaped.

6. The eye protection device of claim 1, wherein the proximal end of the at least one passageway is configured to have an opening upon a generally forward face of the lens frame.

7. The eye protection device of claim 1, wherein the proximal end of the at least one passageway is configured to have an opening upon a generally radially outward face of the lens frame.

8. The eye protection device of claim 1, wherein the at least one passageway follows a generally u-shaped curve with the proximal end configured to have an opening upon a generally forward face of the lens frame.

9. The eye protection device of claim 1, wherein the open face frame is coupled to the lens frame by means of a hinge wherein the hinge is removably detachable from the face and lens frames.

10. The eye protection device of claim 1, wherein the at least one passageway follows an irregular curve with the proximal end configured to have an opening radially outwardly along the perimeter of the lens frame.

11. The eye protection device of claim 1 which additionally includes stiftening element circumscribing the about periphery of said open face frame.

12. The eye protective device of claim 11 wherein said stiffening element is a metal wire.

13. The eye protective device of claim 12 wherein said metal wire is a component of said coupling means and acts to distribute coupling forces.

14. An eye protection device, comprising:
an open face frame;
a lens frame with a lens coupled thereto;
coupling means for coupling the lens frame to the open face frame; and
at least one passageway formed in the open face and lens frames, the at least one passageway having a curved path, wherein the at least one passageway includes a proximal end configured to accept air and a distal end configured to discharge air upon an interior face of the lens and wherein the at least one passageway is tapered along at least a portion of its length whereby the tapered portion functions as a venturi.

15. The eye protection device of claim 14, wherein the curved path of the at least one passageway includes about 20 degrees to about 90 degrees of curvature.

16. The eye protection device of claim 14, wherein the distal end of the at least one passageway is configured to discharge air upon an interior surface of the lens at an angle from a vertical within a range of about 5 degrees to about 85 degrees.

17. The eye protection device of claim 14, wherein the at least one passageway follow a generally unshaped curve.

18. The eye protection device of claim 14, wherein the proximal end of the at least one passageway is configured to have an opening upon a generally forward face of the lens frame.

19. The eye protection device of claim 14, wherein the proximal end of the at least one passageway is configured to have an opening upon a generally radially outward face of the lens frame.

20. The eye protection device of claim 14, wherein the face frame is coupled to the lens frame by means of a hinge wherein the hinge is removably detachable from the open face and lens frames.

21. The eye protection device of claim 14 wherein said coupling means are spaced magnets.

22. The eye protection device of claim 14 wherein said coupling means is a latch.

23. The eye protection device of claim 14 wherein said coupling means is a snap closure.

24. An eye protection device, comprising:
a face frame;
a lens frame with a lens coupled thereto;
a hinge coupling the face frame to the lens frame; and
at least one passageway formed in the face and lens frames, the at least one passageway having a curved path, wherein the at least one passageway includes a proximal end configured to accept air and a distal end configured to discharge air upon an interior face of the lens and wherein the at least one passageway is tapered to form a venturi and wherein the curved path is of generally u-shaped configuration.

25. The eye protection device of claim 24, wherein the generally u-shaped curved path of the at least one passageway includes about 45 degrees to about 90 degrees of curvature.

26. The eye protection device of claim 24, wherein the distal end of the at least one passageway is configured to discharge air upon an interior surface of the lens at an angle from a vertical within a range of about 5 degrees to about 85 degrees.

* * * * *